United States Patent [19]

Luther

[11] Patent Number: 5,112,312
[45] Date of Patent: May 12, 1992

[54] VASCULAR/VENOUS ACCESS DEVICE AND METHOD OF UTILIZING AND FORMING THE SAME

[75] Inventor: Ronald B. Luther, Newport Beach, Calif.

[73] Assignee: Luther Medical Products, Inc., Tustin, Calif.

[21] Appl. No.: 669,679

[22] Filed: Mar. 14, 1991

[51] Int. Cl.⁵ .............................................. A61M 5/32
[52] U.S. Cl. ............................ 604/177; 128/DIG. 26
[58] Field of Search ............... 604/177, 160, 161, 168, 604/174, 282, 178, 179; 128/DIG. 26

[56] References Cited

U.S. PATENT DOCUMENTS

| | | | |
|---|---|---|---|
| 3,225,762 | 12/1965 | Guttman | 604/164 |
| 3,463,152 | 8/1969 | Sorenson | 604/162 |
| 3,630,195 | 12/1971 | Santomieri | 122/DIG. 26 |
| 3,834,380 | 9/1974 | Boyd | 128/DIG. 26 |
| 4,194,504 | 3/1980 | Harms et al. | 604/164 |
| 4,205,675 | 6/1980 | Vaillancourt | 604/164 |
| 4,353,369 | 10/1982 | Muetterties et al. | 604/164 |
| 4,392,856 | 7/1983 | Lichtenstein | 604/177 |
| 4,690,675 | 9/1987 | Katz | 604/177 |
| 4,828,549 | 5/1989 | Kvalo | 604/164 |
| 4,863,431 | 9/1969 | Vaillancourt | 604/168 |
| 4,863,432 | 9/1989 | Kvalo | 604/177 |
| 4,898,591 | 2/1990 | Jang et al. | 604/282 |
| 4,917,671 | 4/1990 | Chang | 604/168 |
| 4,955,863 | 9/1990 | Walker et al. | 604/164 |

FOREIGN PATENT DOCUMENTS 247590 12/1987 European Pat. Off. .... 128/DIG. 26

Primary Examiner—Paul J. Hirsch
Attorney, Agent, or Firm—Stetina and Brunda

[57] ABSTRACT

A vascular/venous access device is comprised of a needle cannula disposed within the central bore at the distal end of a catheter. The distal end of the needle cannula extends outwardly from the central bore at the distal end of the catheter and the proximal end of the needle exits the central bore of the catheter through an aperture or slit formed in the wall of the catheter. A gripping member selectively holds the needle cannula in place within the bore of the catheter during insertion of the needle cannula and catheter into a patient's vascular system. After entry into the vascular system, the needle cannula is withdrawn from the catheter side wall and any desired length of the catheter may then be advanced into the vascular system. The catheter includes a relatively rigid end portion disposed along a substantial length of the needle cannula to prevent buckling and axial compression of the catheter during the insertion process. The comparatively rigid portion rapidly softens upon contact with blood such that a flexible tip is provided for non-traumatic manipulation of the catheter within the vascular system. The catheter may be formed by dipping a mandrel sequentially into polymer material. The distal tip of the expandable material can then be cut from the mandrel, the mandrel removed, and a needle cannula inserted through the side of the catheter such that its sharp tip extends from the open end.

15 Claims, 2 Drawing Sheets

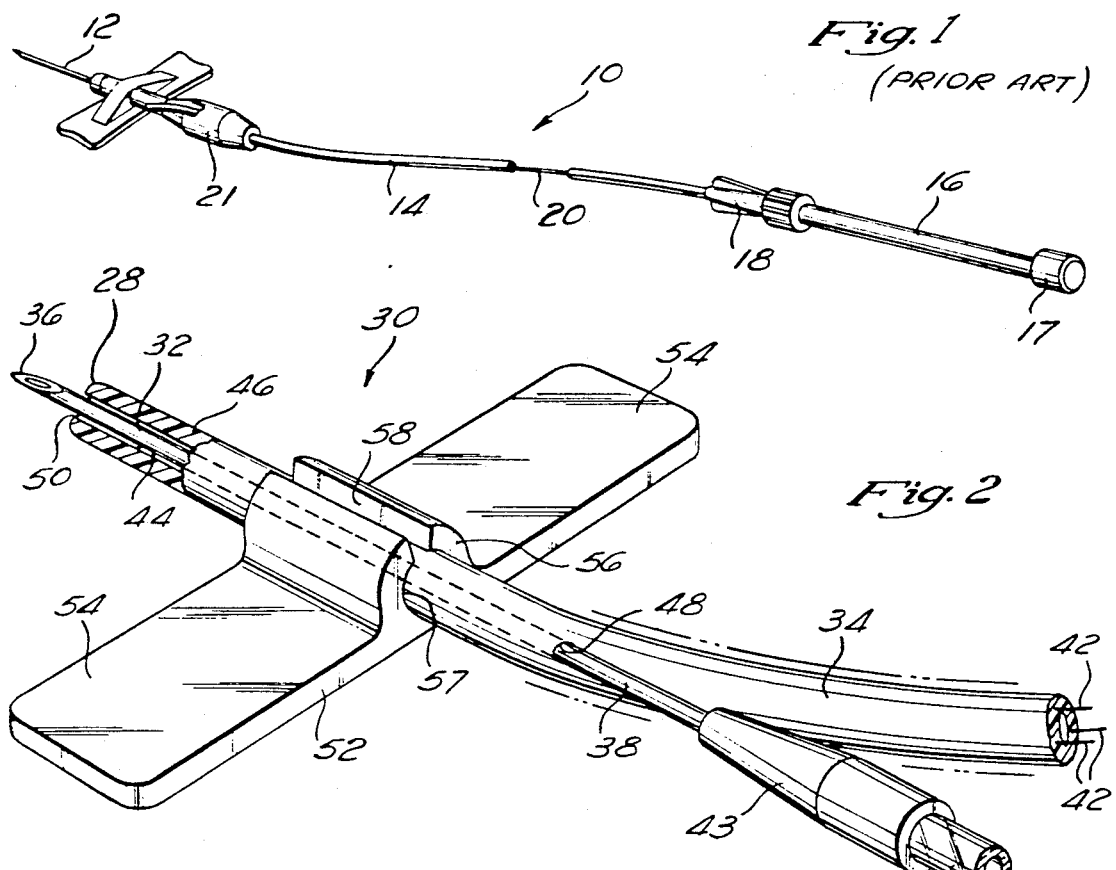
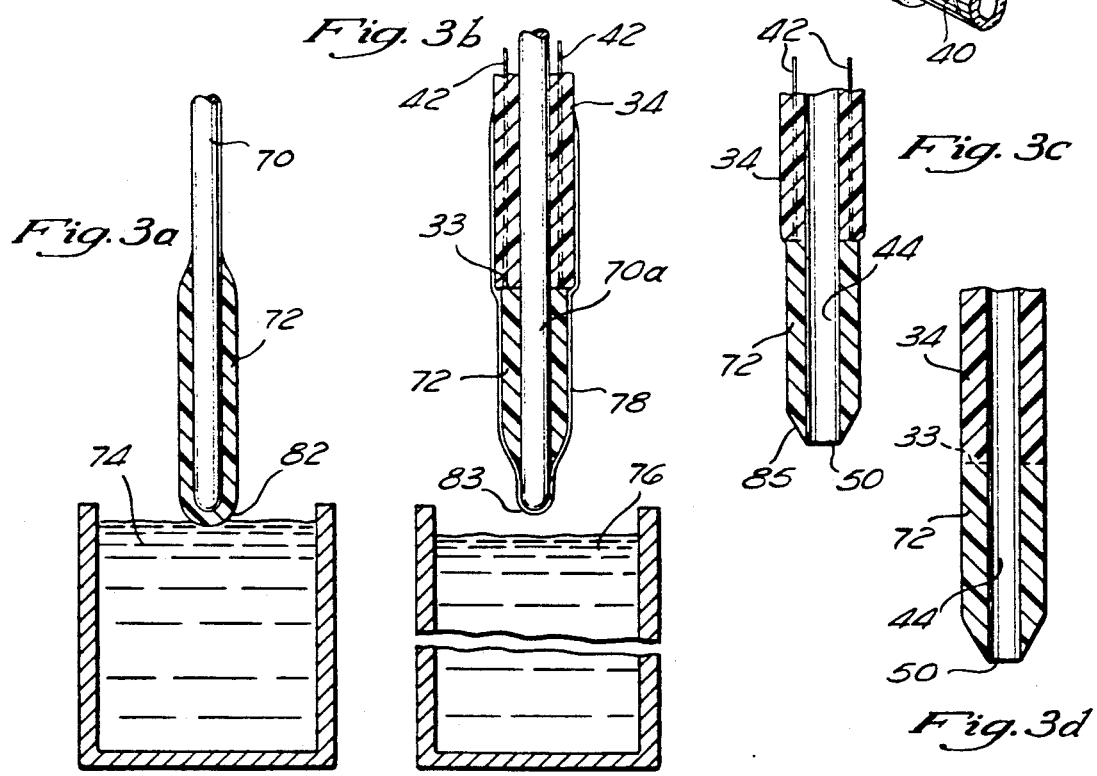

VASCULAR/VENOUS ACCESS DEVICE AND METHOD OF UTILIZING AND FORMING THE SAME

FIELD OF THE INVENTION

The present invention relates generally to medical insertion devices and more particularly to a venous or vascular access device for introducing any desired length of catheter into the vascular system.

BACKGROUND OF THE INVENTION

Vascular venous access devices for introducing catheters into a patient's vascular system are well known. The simplest of such devices comprises a through-the-needle catheter having a cannula which generally comprises a metal needle inserted into the patient's vein and through which a catheter may subsequently be introduced. A common problem associated with the use of such prior art through-the-needle catheter systems arises in removing the cannula after the catheter has been introduced into the vein. Since the cannula is typically comprised of a rigid metal needle, it is desirable to remove the cannula from the patient's vein after insertion of the catheter to prevent trauma to the vein caused by the cannula's rigid structure and/or sharp tip. However, once the catheter has been inserted into the vein, the cannula can typically only be removed by retracting the same upwardly along the catheter, thereby exposing the patient as well as administrating personnel to accidental contact with the cannula.

In recognizing the discomfort and extraction problems of the cannula associated with through the needle catheter systems, over-the-needle catheter systems have been widely utilized for venous access applications. In such over-the-needle catheter systems, a thin catheter having a hub at its proximal end is placed over a rigid cannula, such as a needle, whereby the cannula as well as the catheter may be simultaneously inserted into the vein of a patient. Once the cannula and catheter and have been introduced into the vein, the cannula may be withdrawn from the interior of the catheter leaving the catheter disposed within the patient's vein. Subsequently, required administration line communication can be effectuated with the catheter by interconnection with its hub mounted to the proximal end of the catheter. However, due to such over-the-needle catheters being inserted into the vein of the patient concurrently with the rigid cannula, such over-the-needle catheters must possess sufficient rigidity to prevent the same from traveling axially upward relative the cannula during the insertion process. As such, such over-the-needle catheters are limited in their axial length and are incapable of being inserted upwardly through the length of the vein or artery without causing trauma and/or puncture to the vein.

In recent years, the desirability of utilizing a peripherally inserted central catheter (PICC) line into a patient for medical applications has become widespread. In such PICC line applications, a flexible catheter must be introduced into the vascular system of a patient and subsequently be manipulated to allow the catheter to wind its way upwardly through the vascular system to a desired location. Due to the requirement of advancing the catheter upwardly through the vascular system, the catheter must be formed from a soft, biocompatible, pliable, and flexible material which is capable of winding through and extending through substantial axial lengths of the vascular system. i.e. from two to thirty inches or more, without causing trauma to the vascular system or puncturing therethrough. In view of such requirements, heretofore, through-the-needle catheter systems have been typically utilized wherein after venous insertion, the cannula is retained within the patient and the desired length of catheter is inserted through the cannula and into the vein of the patient. In such applications, blood leakage is commonplace which exposes administrating personnel to substantial health risks, such as that associated with the AIDS virus, hepatitis, and other infectious diseases.

In view of these concerns, recently an over-the-needle catheter system has been introduced specifically adapted for PICC line applications which attempts to minimize accidental exposure of medical personnel to patient's blood. This particular venous access device is manufactured by Menlo Care, Inc. of Palo Alto, Calif. and is marketed under the trademark LANDMARK venous access device.

The LANDMARK venous access device facilitates the insertion of a limited length (i.e. finite length) of catheter into a patient's vein while permitting the needle to be withdrawn after the initial insertion via a stylet extending through the catheter and then stowed within a protective sheath to prevent accidental puncture and/or exposure. However, the LANDMARK venous access device is strictly limited in the length of the catheter provided, thus necessitating the correct initial selection of catheter length. Additionally, the LANDMARK venous access device is relatively complex in its construction, thus increasing the cost of fabrication and consequently increasing its associated patient cost. Furthermore, the LANDMARK venous access device is relatively complicated to use, requiring a significant amount of training and manipulative skill.

In view of the shortcomings of the prior art, it is desirable to provide an improved vascular/venous access device which would permit the introduction of an unlimited length of catheter into a patient's vascular system which facilitates removal of the needle to prevent accidental punctures and/or exposure; which is simple and inexpensive to fabricate; and which requires a minimum of training and manipulative skill to practice.

SUMMARY OF THE INVENTION

The present invention specifically addresses and alleviates the above-mentioned deficiencies associated in the prior art. More particularly, the present invention comprises an improved vascular/venous access device which allows insertion of a flexible over-the-needle catheter of unlimited axial length utilizing a relatively short cannula. The distal or sharp end of the needle cannula extends outwardly from the distal end of the catheter and the proximal end of the needle cannula exits the central bore of the catheter through a hole or slit formed in the side wall a short distance from the distal end of the catheter. A gripping device selectively locks the needle cannula in place within the bore of the catheter and provides a means for gripping the venous access device during insertion of the needle cannula and catheter into a patient's vein, artery, or the like.

The needle cannula provides a rigid and sharp implement for effecting entry into the patient's vascular system. After the needle cannula and catheter have entered the vascular system, the needle cannula is withdrawn from the catheter and the gripping device may be removed or alternatively used as a catheter guide or tape site. The desired length of the catheter may then be manually advanced into the vascular system to a desired position.

The catheter is preferably formed having a generally rigid tip portion disposed along a substantial length of the needle cannula with the remaining length of the catheter being formed having a soft flexible configuration. The rigid portion prevents buckling and/or axial compression of the catheter during the insertion process and subsequently softens upon contact with blood and/or liquids introduced via administration through the catheter or from the thermal gradient caused from patient residence such that a soft flexible tip is then provided for manipulation of the catheter within the vascular system.

The catheter is preferably formed by a sequential mandrel dip process. More particularly, the rigid tip portion may be formed by dipping a mandrel into a solubilized softenable material and allowing the softenable material to dry on the mandrel. The softenable material is preferably hydrated from the mandrel and the desired length for the distal tip portion is cut off. This distal portion is then applied to and dried on a secondary dipping mandrel and a length of flexible catheter is inserted over the mandrel such that the catheter abuts the softenable distal portion. The softenable portion and the portion of flexible catheter are then dipped into a liquid polymer such that the two portions are solvent welded together and an outer layer of polymer is deposited thereover. Thus a contiguous assembly is formed by bonding the softenable material to the distal end of the flexible catheter. The assembly is then allowed to dry and the dipped softenable tip portion is trimmed to exhibit a profile that facilitates insertion into a patient. The mandrel is subsequently removed from the assembly of the catheter and the softenable portion such that a continuous lumen is formed within both portions. A needle cannula is then inserted through the wall of the catheter and extended axially through the length of the catheter such that its sharp tip extends outwardly beyond the softenable end of the catheter.

Thus, the vascular/venous access device of the present invention facilitates the removal and disposal of the needle after introduction of the catheter into the patient's vascular system; permits the introduction of an unlimited length of catheter into the patient; is very simple and inexpensive to fabricate; and requires a minimum of training and manipulative skill to practice. Further, the vascular/venous access device of the present invention allows insertion of any desired length of catheter into a patient utilizing short over-the-needle catheter techniques.

These, as well as other, advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 1 depicts a prior art venous access device wherein the needle may be withdrawn through the catheter and into a sheath;

FIG. 2 is a perspective view of the vascular/venous access device of the present invention;

FIG. 3a is a cross-sectional view illustrating the initial step in forming the catheter utilized in the vascular/venous access device of the present invention;

FIG. 3b is a cross-sectional view illustrating the subsequent steps of forming the catheter utilized in the vascular/venous access device of the present invention;

FIG. 3c is a cross-sectional view of the distal end of the catheter utilized in the vascular/venous access device of the present invention;

FIG. 3d is a cross-sectional view illustrating the swelling of the softenable distal portion of the catheter after having been wet such that the softenable material has become soft and expanded such that the outer diameter thereof has become substantially equal to the outer diameter of the remaining portion of the catheter;

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the function and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Figure 4:
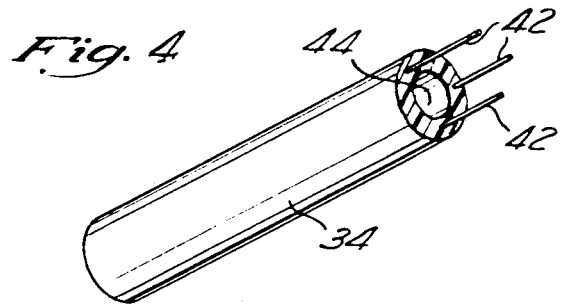
FIG. 4 is a cross-sectional perspective view of the catheter showing a plurality of metal strands disposed within the wall thereof.
Figure 5:
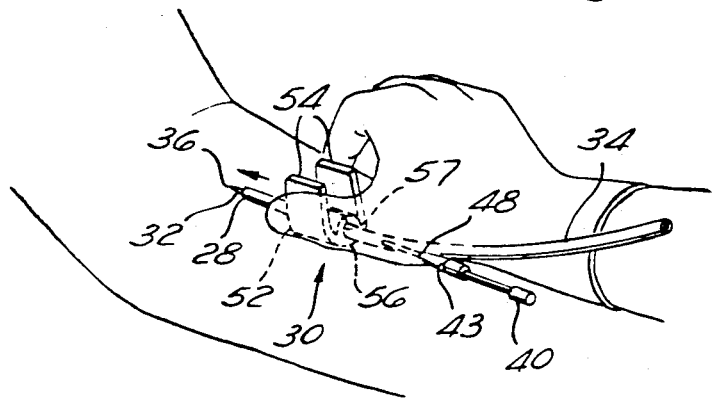
FIG. 5 is a perspective view illustrating insertion of the vascular/venous access device of the present invention into a vein of a patient, showing gripping of the gripper wings to effect locking of the needle cannula within the catheter.
Figure 6:
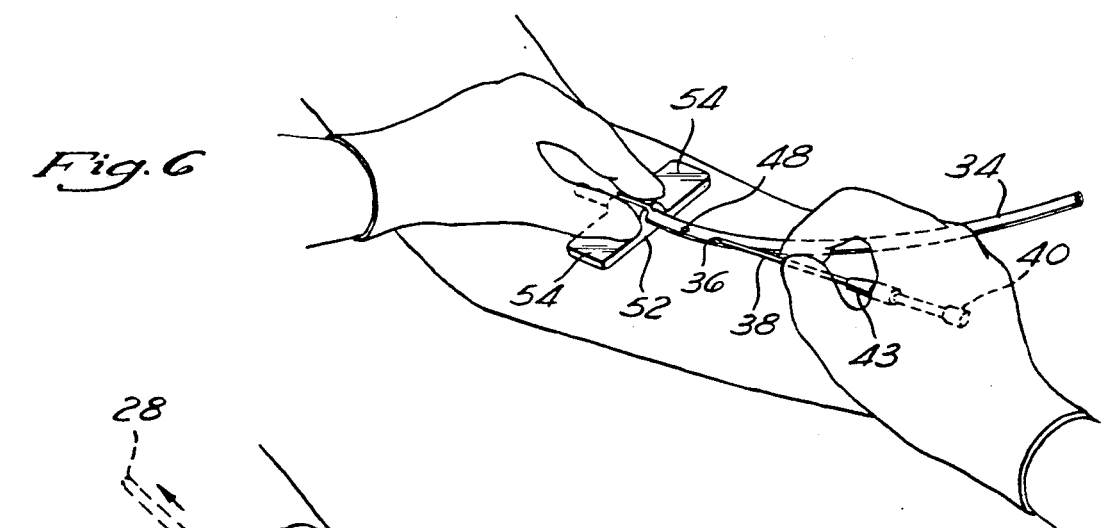
FIG. 6 is a perspective view illustrating withdrawal of the needle cannula from the catheter.
Figure 7:
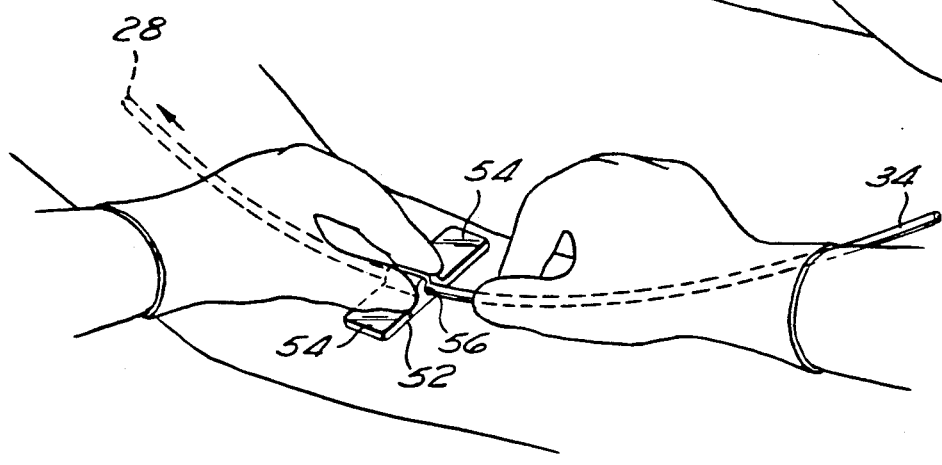
FIG. 7 is a perspective view illustrating advancing of the catheter to a desired axial length within the patient's vein.

The vascular/venous access device of the present invention is illustrated in FIGS. 2-7 with FIGS. 3a-4 illustrating a method for constructing the venous access device and FIGS. 5-7 illustrating its preferred manner of use for peripherally inserted central catheter (PICC) applications. FIG. 1 depicts a prior art venous access device. In this regard, the present invention is applicable to all medical insertion applications. As such, for purposes of this application, the term "venous access device and/or vascular access device" shall encompass all access devices for both venous and vascular applications as well as other medical insertion applications, such as thoracic drain trocar insertion, and similar insertion applications and/or procedures.

Referring now to FIG. 1, a prior art venous access device, known as the LANDMARK venous access device 10 manufactured by Menlo Care, Inc. of Palo Alto, California, is depicted. The LANDMARK venous access device 10 comprises a rigid hollow metal needle 12, a catheter 14, a needle sheath 16, a Luer lock fitting 18, and a wire stylet 20 disposed within the catheter 14 and connected to the needle 12. The LANDMARK venous access device 10 permits venipuncture by use of the needle 12 and subsequently allows retraction of the needle 12 through the catheter 14 and into the sheath 16 by pulling the cap 17 from the sheath 16, thus pulling the wire stylet 20 and the needle 12 through the interior of catheter 14.

After the needle 12 has been withdrawn through the catheter 14 into the sheath 16, the catheter 14 may be manually advanced through the hub 21 into the patient's vein. As will be recognized, the length of the catheter 14 of the LANDMARK device is limited to that length disposed between the hub 21 and the Luer lock 18. Therefore, such a prior art venous access device 10 having a catheter 14 of the correct length must be initially chosen prior to administration upon a patient. If it is determined that the venous access device 10 has a catheter 14 of insufficient length, then the catheter 14 must be removed from the patient's vein and a new venous access device 10 having a catheter 14 of the greater length must be inserted in an analogous venipuncture procedure.

As can be seen from FIG. 1, the prior art venous access device 10 contains numerous molded parts, thereby requiring high tooling costs for manufacture. The comparatively high number of parts also increases materials and assembly costs. As will be appreciated, use of such prior art venous access device 10 further requires substantial training and manipulative ability.

Referring now to FIG. 2, the improved vascular/venous access device 30 of the present invention is depicted. The vascular/venous access device 30 of the present invention comprises a needle cannula 32 disposed within the distal end 28 of a catheter 34 such that the sharp tip or distal end 36 of the needle catheter 32 extends slightly beyond the end opening 50 of the bore 44 at the distal end 28 of the catheter 34. The proximal end 38 of the needle cannula 32 extends through an aperture or slit 48 formed through the wall 46 of the catheter 34. Thus, the needle cannula 32 extends through the distal end 28 of the catheter 34 such that it may be slidably removed therefrom after insertion of the needle 32 and distal end 28 of the catheter 34 into a patient's vein or vascular system.

A gripper member 52 is removably mounted adjacent the distal end 28 of the catheter 34. The gripper 52 includes a pair of wings 54 which facilitate manipulation of the improved vascular/venous access device and a split collet 56 which surrounds a portion of the catheter 34. In the preferred embodiment, gripper 52 is formed of a resilient polymer material so as to be selectively bendable by a user. Additionally, in the preferred embodiment, the insert diameter 57 of the split collet 56 is formed to be slightly greater than the external diameter of the catheter 34 such that the catheter 34 may be axially moved as desired relative thereto. As shown, a groove or gap 58 is additionally formed upon the split collet 56 extending axially along the length of the insert diameter 57. The groove 58 formed in the collet 56 may be expanded by manually bending the wings 54 downwardly toward each other (as viewed in FIG. 2) such that the gripper member 52 may be selectively removed from or installed upon the catheter 34. Bending the wings 54 upwardly (as shown in FIG. 5) causes a reduction in the inside diameter 57 of the collet 56 thereby compressing the catheter 34 such that the needle cannula 32 is retained in place therein and prevented from relative axial movement thereto. A hub adaptor or fitting 43 attaches the proximal end 38 of the needle cannula 32 to a flash tube 40. The flash tube 40 is comprised of a generally transparent tube which is vented to the atmosphere through a filter such that flash blood may be observed therein indicating that the needle cannula has entered the vascular system.

In the preferred embodiment, the catheter 34 is formed of a flexible polymer material capable of being manually advanced within the interior of a patient's vein without causing trauma or puncture thereto. In the preferred embodiment, the flexible material comprises a medical grade, polyurethane polymer. Additionally in the preferred embodiment, a plurality of axially extending wire strands 42 are embedded throughout the length of the catheter 34. Such strands, which are preferably formed of seven-strand stainless steel wire, provide structural bending capability to the catheter 34 such that manipulation of the catheter does not result in substantial bending or kinking of the same while additionally eliminating any axial compression of the catheter during manual advancement in the vascular system of a patient. As additionally shown, the needle cannula 32 travels through the side wall of the catheter 34 via a slit or aperture 48 formed a short distance from the distal end 28 of the catheter 34. In the preferred embodiment, the aperture or slit 48 is formed between two and six inches from the distal end 28 and preferably approximately three to four inches to allow conventional needle cannula lengths to be utilized. Additionally, it will be appreciated that the aperture slit 48 may be formed in the catheter 34 at the time of manufacture or alternatively formed by insertion of the cannula 36 through the side wall of the cannula 34 and into its central cavity 44.

As previously mentioned in the preferred embodiment, the catheter 34 is preferably formed having a generally rigid end portion capable of being inserted into the vascular system of the patient and an extremely flexible remainder portion adapted to permit the catheter 34 to be introduced at desired lengths within the vascular system of the patient. More particularly, the portion of the catheter 34 adjacent its distal end 28, i.e. typically approximately one inch in length, is preferably formed of a hydrophilic polymer material which is comparatively rigid when dry yet softens and expands upon contact with blood. In the preferred embodiment, this particular hydrophilic polymer material comprises a hydrophilic polyurethane, such as that disclosed in U.S. Pat. No. 4,439,583, entitled POLYURETHANE DIACRYLATE COMPOSITIONS USEFUL IN FORMING CANULAE, the disclosure of which is expressly incorporated herein by reference. However, those skilled in the art will recognize that numerous substitute materials possessing such a selective softening property are contemplated herein. More particularly, a suitable material comprises a thermally softening polymer compound which, upon experiencing a thermal gradient such as that encountered between ambient and patient residence temperatures, the polymer rapidly softens and becomes more flexible. An example of such a thermally softening compound is manufactured by Thoratec Laboratories Corporation in Berkeley, Calif. Additionally, in the preferred embodiment the remainder portion of the catheter 34 is formed of a soft flexible polyethylene polymer suitable for non-traumatic travel through the vascular system of the patient. However, those skilled in the art will recognize that alternative polymers are additionally contemplated herein.

In the preferred embodiment, the relatively rigid distal portion of the catheter 34 and remainder portion of the catheter 34 are securely joined together to become a contiguous assembly. During use in veni puncture and central catheter applications, the relatively rigid material at the distal end 28 of the catheter 34 possesses sufficient structural integrity so as to be capable of being inserted within the interior of the patient's vein. Thereafter, upon contact with blood within the vein, the rigid material expands and softens to have a hardness and flexibility substantially equal to that of the remainder portion of the catheter 34 to allow manual advancement of the catheter through the vascular system without causing trauma to the vascular walls and-/or puncture of the same.

Referring now to FIGS. 3a-3c, the preferred method of forming the catheter 34 of the present invention is depicted. With particular reference to FIG. 3a, the comparatively rigid expandable end portion of the catheter 34 is preferably formed by dipping a mandrel 70 having a desired diameter into a quantity of soluble softenable material 74 such that a film or coating 72 is deposited thereon. In the preferred embodiment the coating 72 is applied approximately one-half to one and one-half inches upwardly along the length of the mandrel 70. As used herein, the term "softenable material" refers to a polymer material, such as that disclosed in U.S. Pat. No. 4,439,583, or any other material which, when dry or at ambient temperature, is comparatively rigid and when wet or at elevated temperature becomes more flexible. Subsequently, the coating 72 is allowed to air dry or cure. The dipping and drying processes may be repeated as necessary to attain a coating of the desired thickness (i.e. outside diameter).

The coating 72 of softenable material is preferably hydrated (i.e. removed) from the mandrel 70 and the closed distal tip 82 (shown in FIG. 3a) is cut off and discarded. Subsequently, as depicted in FIG. 3b, the coating 72 of softenable material is inserted upon a secondary dipping mandrel 70a in an axially inverted orientation from that depicted in FIG. 3a. In this inverted orientation, the annular shoulder 33 formed upon the coating 72 by previously cutting off the closed distal tip 82 extends upwardly upon the secondary mandrel 70a while the opposite end of the coating 72 is located upwardly above the end of the mandrel 70a.

With particular reference to FIG. 3b, after the coating 72 of softenable material of the desired thickness has been applied and cured upon the secondary mandrel 70a, a length of preformed hollow flexible catheter material (preferably polyurethane) forming the remainder portion of the catheter 34 is inserted over the opposite end of the secondary mandrel 70a such that it abuts the softenable material 72 at the annular shoulder 33. Subsequently, the coating of softenable material 72 and a portion of the distal end of the flexible catheter 34 are simultaneously dipped into a solvent-based polymer, preferably soluble polyurethane, such that a relatively thin coat 76 thereof is formed to securely attach the coating of softenable material 72 to the remainder portion of the catheter 34 and form a secure assembly capable of eliminating any separation of the rigid end portion and reminder portion of the catheter 34 during use. The entire coating of softenable material 72 and approximately 1 inch of the remainder portion of the catheter 34 are thus coated with polymer 78 as shown in FIG. 3b. The thin coat of polymer 78 preferably comprises a hydrophilic/polyurethane material, i.e. the same material as utilized in forming the coating 72. Subsequently, the lower tip 83 of the polymer 78 may be trimmed to form an opening at the lower end of the coating 72.

As depicted in FIG. 3c, the mandrel 70 is subsequently withdrawn from the bore 44 of the catheter 34 and the end 85 of the softenable material 72 may be trimmed to form the end opening of the bore 44 of the catheter 34 in a suitable configuration for insertion into a patient.

As best shown in FIG. 3c, in the preferred embodiment, the softenable material 72 formed on the end portion of the catheter 34 is preferably sized to have an effective outside diameter slightly less than the diameter of the remainder portion of the catheter 34 and an inside diameter slightly larger than the inside diameter of the remainder portion of the catheter 34. By this procedure, upon the softenable material 72 contacting blood during veni puncture applications, a corresponding expansion or swelling of the same will result due to the hydrophilic property of the polymer material resulting in an increased diameter of the expandable material 72 to have an effective inside and outside diameter substantially equal to that of the remainder portion of the catheter 34, as depicted in FIG. 3d. As such, by proper formation, the resultant catheter length 34 after insertion within the vascular system of a patient and upon expansion of the softenable material 72 will exhibit a constant and generally uniform diameter throughout its length. Additionally, as previously indicated, upon expansion of the softenable material 72, the softenable material 72 softens exhibiting a hardness and flexibility generally commensurate with the remainder portion of the catheter 34.

Referring now to FIGS. 5-7, insertion and use of the improved vascular/venous access device 30 of the present invention is illustrated. For description purposes only, the insertion process is illustrated and described in relation to a venipuncture application. However, as previously stated, the method is additionally applicable to all vascular and medical insertion applications. With particular reference to FIG. 5, the wings 54 of the gripper 52 are initially, manually bent upwardly, such that the inside diameter 57 of the collet 56 and groove 58 (best shown in FIG. 2) of the collet 56 decreases in size, thus collapsing the catheter 34 about the needle cannula 32 and preventing any relative axial movement between the gripper member 52, catheter 34, and needle cannula 32. The wings 54 of the gripper 52 may then be used as a handle to insert the sharp tip or distal end 36 of the needle cannula 32 through a patient's soft tissue and into a vein. Since the softenable material 72 adjacent the distal end of the catheter 34 is dry during insertion, it remains comparatively rigid and therefore resists any axial compression or wrinkling as the needle cannula 32 is inserted into the patient's vein. Flashing of blood in the flash tube 40 visually indicates that the sharp tip or distal end 36 of the needle cannula and catheter 34 has entered the vein.

With particular reference to FIG. 6, after the distal end portion 28 of the catheter 34 has been disposed within the vein, the needle cannula 32 may be withdrawn from the catheter 34. Preferably, the withdrawal of the needle cannula 32 from the catheter 34 is effectuated by releasing the pair of wings 54 and allowing the same to resiliently return to their normally non-deformed position wherein the gripper member 52 assumes a generally planar configuration and the catheter 34 is thus enabled to return to its normal non-collapsed configuration. Subsequently, the wings 54 may be moderately pressed downwardly upon the patient to maintain the gripper member 54 and catheter 34 stationary relative the patient while the needle cannula 38 may be withdrawn within the interior of the cannula 34 outwardly through the aperture or slit 48 in a direction indicated by the arrow in FIG. 6. Due to the flexibility of the remainder portion of the catheter 34 as well as low pressure (i.e. ambient pressure conditions) existing within the interior 44 of the cannula 34, the aperture or slot 48 substantially occludes itself, i.e. closes, to prevent any blood traveling axially within the interior of the catheter 34 from exiting therefrom. As such, inadvertent contact with blood by administrating personnel is substantially avoided. Additionally, it will be recognized that once the needle cannula 38 has been removed from the catheter 34, it may be rapidly disposed of in a conventional sharps container to avoid any inadvertent contact to the patient or administrating personnel. Alternatively, it additionally will be recognized that the needle cannula 38, hub 43, and flashback chamber 40 may be included as a portion of one of the more recently introduced "stickless needle cannula" syringes and/or catheter devices wherein the needle cannula 38 may be retracted into a protective sleeve to prevent any inadvertent contact to the patient or administrating personnel. Examples of such a "stickless needle cannula system" is shown in U.S. Pat. Nos. 4,762,516, 4,832,696, and 4,950,252, assigned to the subject assignee.

Since the softenable portion 72 adjacent the distal end 28 of the catheter 34 has been introduced into the vein of the patient and has resided therein for a short period of time, the softenable material 72 has been exposed to blood wherein the softenable material 72 has expanded or swelled to assume an outside diameter substantially equal to the outside diameter of the remainder portion of the catheter 34 as depicted in FIG. 3d. Additionally, during this expansion or swelling of the softenable material 72, the softenable material 72 has softened to possess a softness and flexibility generally commensurate with the remainder portion of the catheter 34. As such, the catheter 34 may now be manually advanced into the vein of the patient without causing trauma or puncture of the vein of the patient.

In the preferred embodiment, the advancement of the cannula 34 within the vein of the patient is accomplished by holding the gripper member 52 stationary upon the patient and sliding the catheter 34 through the collet 56 of the gripper 52. As will be recognized, due to the inside diameter 57 of the collet 56 being slightly greater than the outside diameter of the catheter 34, the catheter 34 may be easily extended axially through the collet 56 with the collet 56 forming a catheter guide facilitating ease of insertion of the catheter 34 into the vein of the patient. Alternatively, if desired the gripper 52 may be removed from the catheter 34 and discarded. The length of the catheter 34 which may be fed into the patient's vein is limited only by the amount of catheter 34 available. Thus, the administrating personnel does not have to carefully choose the length required prior to insertion of the needle 32 and catheter 34 nor is insertion length limited to the length of any internal stylet as utilized in the prior art. Rather, any desired length can be uncoiled from a sealed sterile enclosure.

As will be recognized, during manual advancement of the catheter 34 into the vein of a patient, the catheter 34 is free to probe and extend upwardly within the vein without puncturing or causing trauma to the vein due to the soft distal end portion 20 of the catheter 34. Further, during manual advancement of the catheter 30 to a desired position within the vein, the catheter is prevented from inadvertently kinking or axially compressing due to the plural elongate wire strands 42 embedded within the wall of the catheter 34. As will be recognized, due to such wire strands being formed of stainless steel and captured within the interior of the catheter 34, the same provides sufficient structural rigidity to prevent kinking of the catheter while enabling desirable flexibility of the catheter 34 necessary to enable the catheter 34 to wind through the interior of the vein without damage thereto.

When the distal end 28 of the catheter 34 is advanced to its desired location within the vein, the gripper member 54 may be utilized as a tape site to maintain the catheter 34 at its desired central position upon the patient. Additionally, due to the plural strands or wires 42 disposed within the interior of the catheter 34 being radio opaque, conformation of the desired position of the distal end 28 of the catheter 34 within the patient may be confirmed using conventional imaging techniques. Subsequently, the proximal end of the catheter 34 may be connected to conventional IV tubing or the like via conventional heparin looks and/or Luer lock connections for administration of general IV therapy solutions, administration drugs, blood samplings, and the like.

It is understood that the exemplary venous access device described herein and shown in the drawings represents only a presently preferred embodiment of the invention. Indeed, various modifications and additions may be made to such embodiment without departing from the spirit and scope of the invention. For example, the gripper need not be a generally planar device, as illustrated, but rather may be any configuration which readily facilitates manipulation of the catheter 34 and needle 32 while locking them together. Also, the softenable material and polymer need not be necessarily formed by being applied to a mandrel and sequential dipping as illustrated. Rather, various means of application are suitable. Further, the softenable material need not necessarily expand upon contact with blood but rather merely soften upon contact with blood. Thus, these and other modifications and additions may be obvious to those skilled in the art and may be implemented to adapt the present invention for use in a variety of different applications.

Further, those skilled in the art will recognize that in a broad sense the present invention discloses an insertion system for inserting a peripherally inserted central catheter line by use of a short over-the-needle catheter administration technique. This is accomplished in the present invention by the substantial recognition by the subject applicant that the needle cannula 38 may be inserted into the interior of the catheter via the slot or aperture 48 formed in the side wall of the same without substantially adversely affecting the function of the catheter 34. Additionally, by forming the distal end or tip of the catheter 34 from an initially more rigid material to enable insertion into the vascular system of the patient and subsequently allowing the same to soften upon exposure to patient blood, the catheter can be readily manipulated through the vascular system of the patient without trauma or puncture of the vascular system. As such, the present invention enables the use of a catheter having unlimited length to be introduced into a patient by use of short needle, over-the-needle catheter insertion techniques which heretofore have been unavailable in the prior art.

What is claimed is:

1. A vascular/venous access system comprising:
   (a) a flexible catheter having a distal end and a proximal end and an axial bore extending therethrough, a portion of said catheter located at the distal end of said catheter being formed of material having greater rigidity than the remainder of said catheter; and
   (b) a needle cannula disposed within the bore adjacent the distal end of the catheter with the sharp end of the needle cannula extending outwardly beyond the distal end of the catheter and the opposite end of the needle extending through the wall of the catheter between the distal end and proximal end of the catheter.

2. The vascular/venous access system as recited in claim 1 wherein said portion of said cannula is formed of a material which softens when exposed to blood such that the portion of the catheter is generally rigid during insertion of the catheter into a vein of a patient and becomes more flexible after the catheter resides in the vein.

3. The vascular/venous access system as recited in claim 2 further comprising a gripper member engageable with said catheter for selectively preventing relative axial movement between said catheter and said needle cannula, said gripper member comprising:
   (a) a collet which surrounds a portion of said catheter;
   (b) a pair of handles attached to said collet and configured such that said handles may be manually bent together to cause said collet to selectively collapse said catheter about said needle cannula; and
   (c) a groove formed in said collet such that said pair of handles may be manually bent to cause the groove to open such that said collet may be repositioned upon said catheter.

4. The vascular/venous access system as recited in claim 3 wherein said catheter further includes a plurality of wires extending axially within the wall of said catheter.

5. The vascular/venous access system as recited in claim 4 wherein said wires comprise multi-strand stainless steel wire.

6. The vascular/venous access system as recited in claim 5 further comprising a layer of polymer substantially covering the portion of said catheter and an adjacent portion of the remainder of said catheter.

7. The vascular/venous access system as recited in claim 6 further comprising a flash chamber in fluid communication with said needle cannula adjacent the opposite end of said needle cannula.

8. The vascular/venous access system as recited in claim 7 wherein said portion of said catheter is comprised of hydrophilic polyurethane.

9. The vascular/venous access system comprising:
   (a) a flexible catheter having a distal end and a proximal end and an axial bore extending therethrough;
   (b) a needle cannula disposed within the bore adjacent the distal end of the catheter with the sharp end of the needle cannula extending outwardly beyond the distal end of the catheter and the opposite end of the needle extending through the wall of the catheter between the distal end and proximal end of the catheter;
   (c) a gripper member engageable with said catheter for selectively preventing relative axial movement between said catheter and said needle cannula, said gripper member comprising:
      (i) a collet which surrounds a portion of said catheter;
      (ii) a groove formed in said collet such that said pair of handles may be manually bent to cause the groove to open such that said collet may be repositioned upon said catheter; and
      (iii) a pair of handles attached to said collet and configured such that said handles may be manually bent together to cause said collet to selectively collapse said catheter about said needle cannula.

10. The vascular/venous access system as recited in claim 9 further comprising a portion of said catheter located at the distal end of the catheter being formed of material having greater rigidity than the remainder of said catheter.

11. The vascular/venous access system as recited in claim 10 wherein said portion of said cannula is formed of a material which softens when exposed to blood such that the portion of the catheter is generally rigid during insertion of the catheter into a vein of a patient and becomes more flexible after the catheter resides in the vein.

12. The vascular/venous access system as recited in claim 11 wherein said catheter further includes a plurality of wires extending axially within the wall of said catheter.

13. The vascular/venous access system as recited in claim 12 wherein said wires comprise multi-strand stainless steel wire.

14. The vascular/venous access system as recited in claim 13 further comprising a layer of polymer substantially covering the portion of said catheter and an adjacent portion of the remainder of said catheter.

15. The vascular/venous access system as recited in claim 14 further comprising a flash chamber in fluid communication with said needle cannula adjacent the opposite end of said needle cannula.

* * * * *